United States Patent
Litvak

(10) Patent No.: US 7,217,371 B2
(45) Date of Patent: May 15, 2007

(54) OPTICAL CONTROL INTERFACE BETWEEN CONTROLLER AND PROCESS CHAMBER

(75) Inventor: Herbert E. Litvak, San Jose, CA (US)

(73) Assignee: Lightwind Corporation, San Francisco, CA (US)

( * ) Notice: Subject to any disclaimer, the term of this patent is extended or adjusted under 35 U.S.C. 154(b) by 218 days.

(21) Appl. No.: 10/898,891

(22) Filed: Jul. 26, 2004

(65) Prior Publication Data

US 2005/0078300 A1    Apr. 14, 2005

Related U.S. Application Data

(60) Provisional application No. 60/490,369, filed on Jul. 25, 2003.

(51) Int. Cl.
*G01R 31/00* (2006.01)

(52) U.S. Cl. .................... 216/60; 216/61; 216/59; 216/79; 216/85; 438/710; 438/740; 356/226; 356/216; 356/302; 356/450; 356/225; 356/139.1

(58) Field of Classification Search ............... 216/60, 216/61; 438/710, 740; 356/226, 216
See application file for complete search history.

(56) References Cited

U.S. PATENT DOCUMENTS 6,366,346 B1 * 4/2002 Nowak et al. ............ 356/72

OTHER PUBLICATIONS

S.Wolf, Silicon Processing for the VLSI Era, vol. 1, Lattice Press (1986), p. 567.*

* cited by examiner

*Primary Examiner*—Nadine Norton
*Assistant Examiner*—Maki Angadi
(74) *Attorney, Agent, or Firm*—Ernest J. Beffel, Jr.; Haynes Beffel & Wolfeld

(57) ABSTRACT

The present invention relates to interfacing new sensors to incumbent controls. In particular, it relates to optically interfacing a new sensor, such as a spectrometer with plasma generator, to an incumbent electro-optical sensor. Logic and resources to control activation of the incumbent electro-optical sensor may be included. Particular aspects of the present invention are described in the claims, specification and drawings.

13 Claims, 3 Drawing Sheets

OPTICAL CONTROL INTERFACE BETWEEN CONTROLLER AND PROCESS CHAMBER

RELATED APPLICATIONS

This application claims the benefit of a provisional application filed on 25 Jul. 2003, application Ser. No. 60/490,369, entitled "Optical Control Interface Between Process End Point Controller and Plasma Etcher" by inventor Herbert E. Litvak, which provisional application is hereby incorporated by reference.

This application is related to provisional applications filed on 25 Jul. 2003, application Ser. No. 60/490,084, entitled "Method and Apparatus for Chemical Monitoring of Atomic Layer Deposition (ALD) Processes" by inventor Herbert E. Litvak; application Ser. No. 60/490,372, entitled "Method and Apparatus for Optical Emission Leak Detection in Vacuum Systems" by inventors Herbert E. Litvak and Gary B. Powell; and application Ser. No. 60/490,113, entitled "Method and Apparatus for Monitoring Chemical Utilization/Efficiency in Chemical Processing Equipment" by inventors Herbert E. Litvak and Gary B. Powell, which provisional applications are hereby incorporated by reference.

This application incorporates by reference the International Application No. PCT/US01/44585 entitled "Method and Device Utilizing Plasma Source for Real-Time Gas Sampling" filed in the U.S. Receiving Office on 29 Nov. 2001 designating the U.S. and other countries and published in English, which claims the benefit of U.S. application Ser. No. 10/038,090 filed by inventors Richard L. Hazard and Gary Powell on 29 Oct. 2001 and U.S. application Ser. No. 09/726,195 filed by Applicant Lightwind Corporation and inventor Gary Powell on 29 Nov. 2000; and incorporates by reference U.S. application Ser. No. 09/631,271 entitled "Inductively Coupled Plasma Spectrometer for Process Diagnostics and Control" filed by inventor Gary Powell on 2 Aug. 2000.

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

The present invention relates to interfacing new sensors to incumbent controls. In particular, it relates to optically interfacing a new sensor, such as a spectrometer with plasma generator, to an incumbent electro-optical sensor. Logic and resources to control activation of the incumbent electro-optical sensor may be included.

Semiconductor manufacturing has adopted various telemetry techniques utilizing mass spectrometry or process plasma glow spectrographic analysis to improve the cleaning, conditioning or operation of reaction chambers in which a variety of reactions take place, such as deposition, cleaning, etching, implantation, ashing, etc. Telemetry techniques help operators monitor processes that take place on a microscopic level inside a closed chamber that often is sensitive to any form of outside radiation. One technology sometimes used is monitoring a plasma reaction chamber to view radiation emitted by process plasma. Another technology is to use a mass spectrometer to analyze residual gases. More recently, these inventors have begun using a spectrometer having a plasma generator to analyze process gases.

An opportunity arises to interface new sensors with incumbent sensors. A way of coupling the new sensors that would provide familiar signals to incumbent sensors may be integrated to a facility more easily than an entirely new system.

SUMMARY OF THE INVENTION

The present invention relates to interfacing new sensors to incumbent controls. In particular, it relates to optically interfacing a new sensor, such as a spectrometer with plasma generator, to an incumbent electro-optical sensor. Logic and resources to control activation of the incumbent electro-optical sensor may be included. Particular aspects of the present invention are described in the claims, specification and drawings.

DETAILED DESCRIPTION

Figure 1:
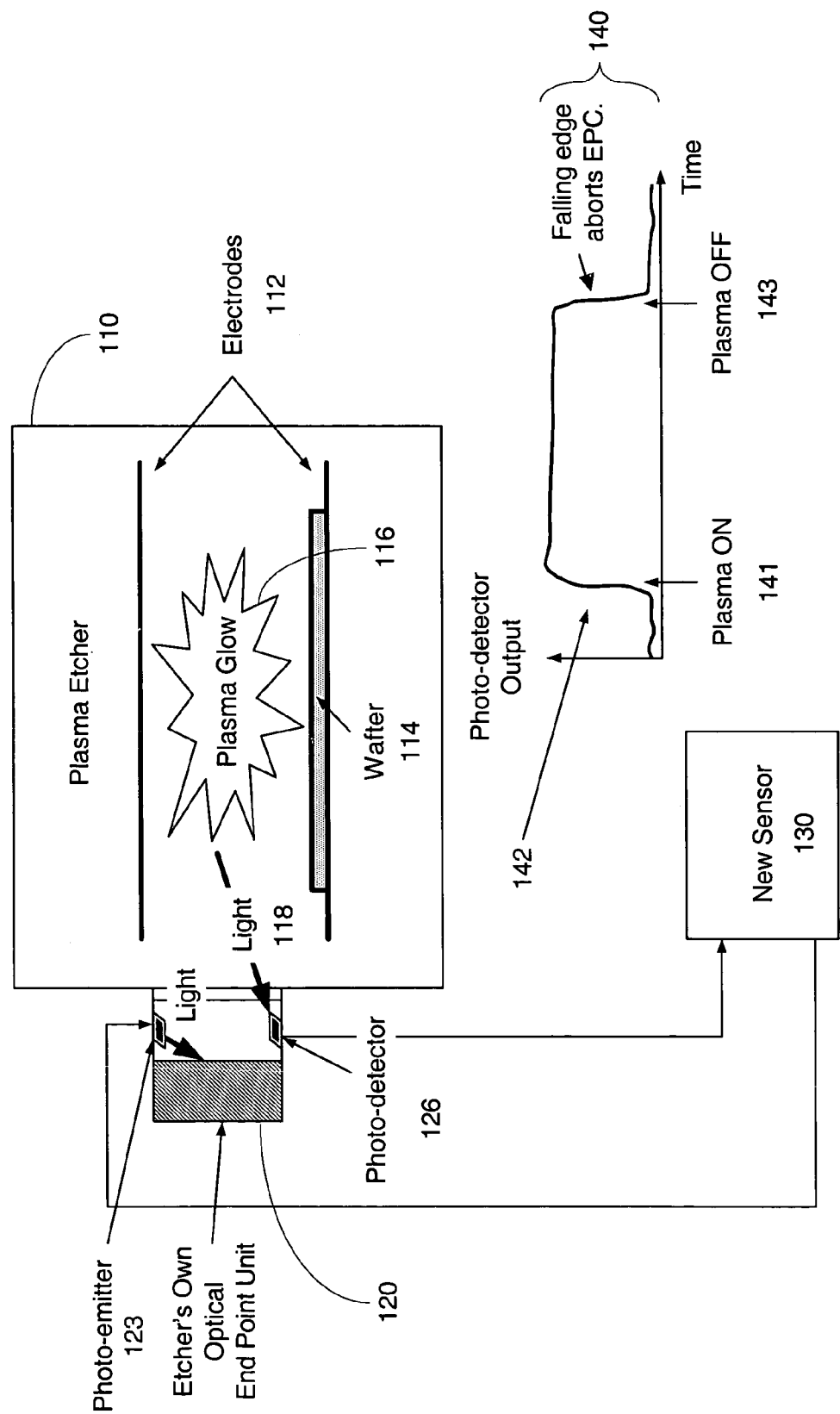
FIGS. 1 and 2 provide a schematic and close-up schematic of an all-optical interface between old and new sensors.

The following detailed description is made with reference to the figures. Preferred embodiments are described to illustrate the present invention, not to limit its scope, which is defined by the claims. Those of ordinary skill in the art will recognize a variety of equivalent variations on the description that follows.

On many semiconductor vacuum-processing systems, sensors are used to detect changes in their processes. Those sensors send information that is processed by software to terminate or modify the process when predetermined and measured changes occur. The method of terminating the process is referred to as "endpoint" on many tools.

The incumbent endpoint software algorithm has many variations but a typical embodiment consists of an initialization or self-referencing step followed by a step where a change in sensor signal increases or decreases. The decrease or increase in the signal connotes that the process should be stopped or altered when it reaches a predetermined value or rate of change. In this context, the sensor signal typically corresponds to detected process plasma glow.

As sensors and software improve, there is a requirement to replace the incumbent devices with more effective ones, and to then communicate the information with the process tool.

To be fully effective, an external End Point Controller, "EPC", must have a communications interface with the plasma etcher (host tool) being monitored. The purpose of this communications interface is, for instance, for the etcher to provide a "Start of Process" signal to the EPC, so that it can begin monitoring the process for End Point, and/or for the EPC to communicate the "Process End Point Detected" or "Stop Etch" condition to the etcher.

The communications interface between an EPC and a tool is generally implemented either as an electrical interface or using software messages. In an electrical hardware interface (e.g. TTL or other logic level control signals), a change in electrical voltage is interpreted as either a tool or process state change. A software-messaging interface (using e.g., SECS/GEM or TCP/IP protocols) uses information-containing message strings to pass information to a tool or its process controller.

Integrating a new sensor with an electrical hardware interface or software message interface may present implementation challenges. The first will require knowledge of and possibly interruption of existing electrical connections, while the second may require writing of extensive and detailed computer code. Both techniques may thus be time-consuming to implement, and may impact tool reliability, for instance, if hardware or software implementation errors are made. Furthermore, the interface, once implemented, is usually quite specific for the make and model of the etcher. Wholly different interfaces may be required for etchers of different manufacturers or models.

A further problem in the semiconductor industry is retrofitting controls to equipment without voiding the warranty of the equipment manufacturer. Most often, the warranty or service contract will be impacted by changes in the electrical or software configuration of the system. Therefore, there is an opportunity to retrofit systems by tricking existing sensors, such as electro-optical sensors provided with the system, to signal process conditions monitored and detected by retrofitted sensors. The opportunity is to use existing inputs and controls with a new sensor, without modifying the system in a way that would complicate warranties or service.

An optical interface can provide a variety of signals used for process control. A "Process Start" signal can be provided using a new sensor that includes a simple photo-detector (e.g. photodiode or similar device), which will exhibit a very large electrical signal change as the plasma ignites and begins to emit substantial amounts of optical emission radiation (from the "plasma glow"). Since most commercial etch tools are provided with an optical emission-based EPC, as well as software logic to interpret changes in the optical emission intensity as an "End Point Detected" condition, an optical interface can mimic a plasma optical emission for "Process Start" or "End Point Detected" condition by means of an external light source (e.g. Light Emitting Diode, LED, or other photo-emitter), whose intensity can be switched high or low (as required for the specific etcher). It is generally very easy to configure the End Point detection software of the etcher to recognize the very large change in photo-emitter intensity, and discriminate against any changes in the plasma optical emission. Logic can be supplied within the EPC to accommodate multi-step etch processes (e.g. when a fixed time over-etch immediately follows a main etch, whose End Point has been detected by the external EPC), as well as etcher fault conditions (e.g. premature plasma shut-off). Additionally, programming of the etcher to ignore "Stop Etch" outputs from the EPC can prevent unwanted EPC control during break-through or over-etch steps.

The solution disclosed uses optical coupling to the etcher (i.e. no electrical or logic interface is required), and software-programmed logic residing within the EPC. Some standard configuring of the etcher's process or end point recipe steps may also be required. However, no new logic or programming of etcher software should be required. This solution is not only much simpler to implement than traditional electrical or logic-based interfaces, but is more general in the sense that no detailed knowledge of etcher-specific interfaces is required. The etcher-specificity may extend no further than a customized opto-mechanical mount for the LED and photo-detector.

Figure 2:
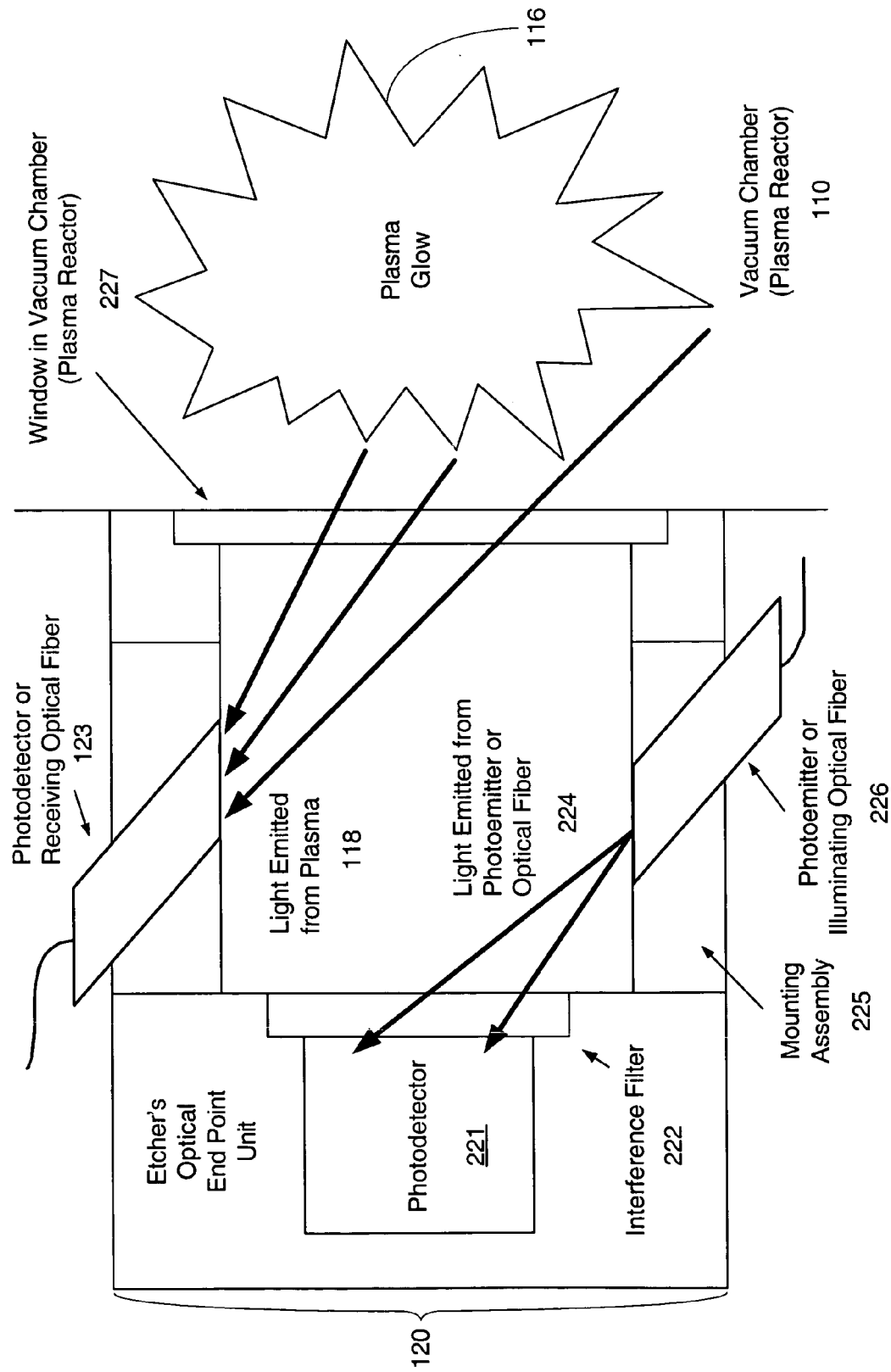

FIGS. 1 and 2 provide a schematic and close-up schematic of an all-optical interface between old and new sensors. In FIG. 1, a plasma chamber 110, such as a plasma etcher chamber, is depicted. Electrodes 112, in some configurations, energize plasma 116. The electrodes may be internal or external, without affecting application of the technology disclosed. The purpose of the glowing plasma is to interact with the wafer 114 or materials that interact with the wafer. That is, the wafer does not need to be positioned between the electrodes or within the plasma region for this interface to work. A consequence of plasma glow is emission of light 118. Outside the reaction chamber, an end point unit 120 is positioned to collect light from the plasma glow. Details of the end point unit 120 are supplied in FIG. 2. Endpoint control logic 130 of the new sensor controls a photoemitter or illuminating optical fiber 126, and is optionally coupled to a new photodetector 123.

FIG. 2 provides additional detail of interfacing an incumbent sensor including a photodetector 221 with a new sensor 130. The incumbent optical endpoint sensor optionally includes an interface filter 222. The filter may be used to help tune the photodetector to emissions from the new photo emitter 126, attenuating the light emitted from the plasma 118. A mounting assembly 225 moves the photodetector 221 away from the window in the vacuum chamber 227. Depending on the view angle, this mounting assembly may reduce the incidence of light 118 from the plasma glow 116 hitting the photodetector 221. Directing a photo emitter or illuminating optical fiber 126 at the photodetector 221 accomplishes an interface with photodetector 221 of the incumbent sensor. Optionally, a photodetector or receiving optical fiber 123 also may be added to the mounting assembly 225 to sense light 118 from the plasma glow. When a spectrometer with plasma generator is used as the new sensor, the photodetector or receiving optical fiber 123 may optionally provide redundancy, but is not necessary.

Figure 3:
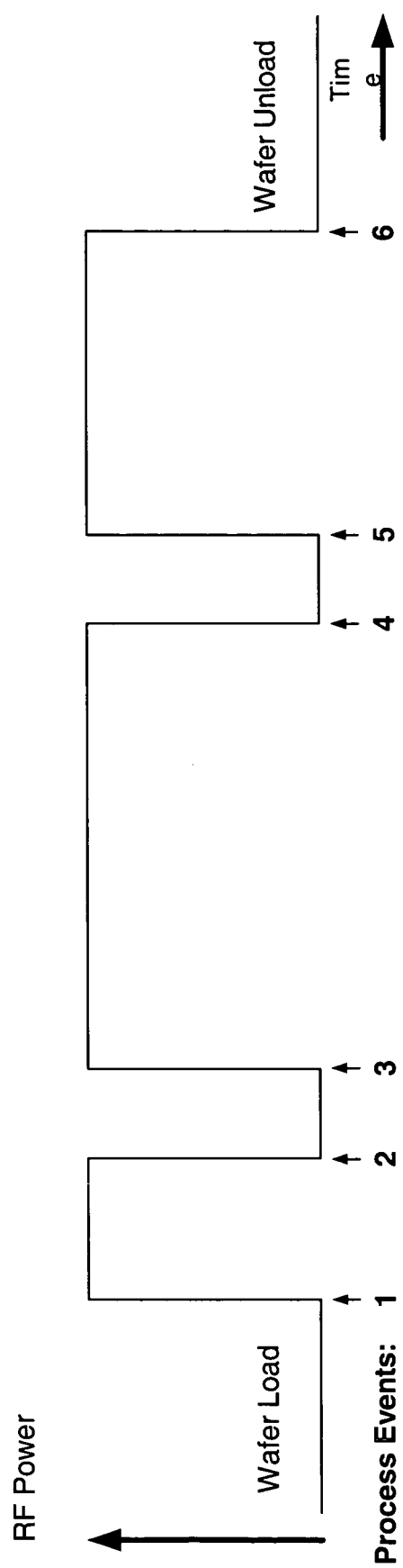
FIG. 3 depicts a typical etcher with endpoint controller process sequence. The vertical axis of this figure is RF power used to energize a plasma.

FIG. 3 depicts a typical etcher with endpoint controller process sequence. The vertical axis of this figure is RF power used to energize a plasma. The horizontal axis is time, not necessarily to scale. Prior to event 1, a wafer is loaded into the plasma chamber. At event 1, the RF power is increased. This is a so-called breakthrough step, which typically lasts 10 to 30 seconds. The etcher controls this step. The new sensor may be searching for an endpoint condition, but the process controller should ignore any signal from the new sensor that suggests an endpoint during the breakthrough step. Alternatively, the new sensor can be programmed to delay its search for a reaction end point until some minimum process time has elapsed, effectively ignoring the breakthrough step and potentially ignoring short etch steps. Event 2 is a plasma off event, in case the process requires an interruption of plasma generation, for instance while an etching component is introduced to the reaction chamber. Event 3 is a plasma on event, for the main etch step. The main etch step typically lasts 60 to 180 seconds. During this time, the new sensor and its endpoint logic are detecting a condition that signals an end of the reaction. When the condition is detected, or the etcher times out, the plasma is turned off at event 4. In normal operation, the new sensor and endpoint logic signal the incumbent process controller through the incumbent photodetector 221 to turn off the plasma. Events 5 and 6 are an example of an over-etch step, in which a controlled amount of etching beyond the detected endpoint is performed, for instance to remove rounded sidewall corners at the bottom of a trench.

At event 5, the over-etch step begins. The new sensor and endpoint logic either are programmed to ignore the over-etch step or they produce output that is ignored by the incumbent process controller. This is because the nature of an over-etch step is to etch for a certain time after an endpoint condition is detected. Alternatively, the over-etch step could be performed without the plasma off and on the events 4 and 5. After event 6, and the completion of over-etching, the wafer may be unloaded or otherwise processed.

The present invention is operable with a variety of sensors that include endpoint detection logic, including spectrometer systems. One new sensor that can be interfaced with an incumbent optical sensor or EPC includes a spectrometer with a plasma generator and an array of detectors. The plasma source includes an excitation chamber and external electrodes. The chamber may be made of a variety of materials that are compatible with a range of processes being monitored. Etch reactions typically require corrosive gases and significantly affect excitation chamber material choices. A quartz chamber, for instance, is unlikely to be compatible with etch processes containing fluorine, because quartz is etched by fluorine. Ceramics, such as high purity aluminum oxide (sometimes called alumina) or sapphire, are suitable for monitoring fluorine etch processes. Ceramics having substantial silicon content are less desirable, because fluorine or chlorine can remove the silicon. Boron carbide and nitride are other ceramics that resists fluorine and chlorine and might be used as a structural or coating material. Zirconia is another ceramic that may have the desired characteristics. Generally, any ceramic-like material that is compatible with sustained exposure to fluorine or other halogen-based reactive chemical gases could be used to build a chamber. Preferably, the ceramic-like material should be compatible with both fluorine and chlorine etching. An excitation chamber preferably has a small volume, such as 40–70 cubic centimeters, as power requirements are low per volume and it is preferred to use a low power level to sustain a plasma discharge. Low power requirements eliminate the need for water or forced air cooling, which may be used in alternate embodiments. Low power requirements tend to extend the lifetime of components. Typical power requirements depend on the process, which the system is monitoring. Power levels of 15 to 75 watts are suitable for a wide range of monitoring tasks. Power levels of 50 to 75 watts are suitable for monitoring a higher pressure process, above 1 torr, such as a stripping process. Power levels of 20 to 50 watts are suitable for monitoring etch and deposition processes. Power levels as low as 5 to 20 watts could be used if the plasma excitation chamber were reduced in size to a volume of approximately 5 to 15 cubic centimeters. A smaller chamber in the volume range of 1 to 5 cubic centimeters could be used although gas transport at pressures below 150 millitorr may reduce its responsivity. It is desirable for the power setting to be software controlled and adjusted automatically to modify the light emission from the plasma. The software can evaluate the light emission at a-chosen wavelength or set of wavelengths during a chosen stage of operation and adjust the power to generate the desired light emission. Alternatively, recipes can be developed based on experience that includes particular power levels for particular circumstances where the software can automatically step through sequences that match the state or condition of the process operation. The power adjustment impacts the overall instrument sensitivity. This provides a second way to increase system sensitivity to spectral emissions.

The plasma source can use a range of RF frequencies for excitation. One useful frequency is 13.56 MHz +/−1 MHz, which is an unlicensed operating band. Other frequencies from 1 MHz to 900 MHz are also useful. At the low end of the range, frequencies of 1 MHz or greater require less driving voltage to generate a plasma. At the upper end, the response of the ions and electrons to the excitation frequency changes their behavior. Within the overall range, other frequencies are available. Those frequencies that do not require licensing are preferable. Use of the predominate 13.56 MHz drive frequency generates a familiar spectral output. Other frequencies that also may be used include 27 and 40 MHz Excitation frequencies below 1 MHz can cause increased erosion (sputtering) of electrode materials and therefore reduced source lifetimes. Frequencies at or above 1 MHz are more efficiently coupled through dielectrics such as quartz or ceramics. External electrodes can be problematic to implement below 1 MHz with ceramic or anodized aluminum excitation chambers, for instance. A requirement for plasmas powered by external electrodes is efficient power transfer through the dielectric. Many applications use gases that chemically attack source materials or walls. In using materials that are chemically durable, excitation frequencies above 1 MHz couple power more effectively into the plasma. Frequencies above 900 MHz can be harder to ignite. A preferred range of operating frequencies is about 13 to about 40 MHz.

The source can operate from below 5 millitorr to above 5 torr without requiring pressure control or additional pumping while requiring minimal power input.

The window material through which the spectra are transmitted is made of sapphire because of its resistance to most process chemistry. A secondary issue is the deposition of sampled gas byproduct on the sapphire window. When the plasma source for the spectrometer has the capability of having reducing or other reactive gases added directly to it, those gases may be ionized and act in a manner to keep the spectral transmission window clean. This secondary gas input allows the use of the gases without contamination or effect on the actual process chamber.

A variety of detector arrays can be used with this invention, as described more fully in the disclosures incorporated herein by reference.

The present invention may be practiced as a method or a device that includes components that are adapted to practice the method. The same method can be viewed from the perspective of emitting a signal, controlling a process or making a structure in a layer of a semiconductor device.

One embodiment is a method of retrofitting a process chamber control system. The system to be retrofitted includes a process chamber and an incumbent electro-optical sensor that is optically coupled to a plasma glow region in the process chamber and operably coupled to process controls for the process chamber. This method includes monitoring exhaust gases from the process chamber in a device outside the process chamber, utilizing a spectrometer having a plasma generator and detecting at least one spectrometer plasma emission signal. Alternatively, other types of new or updated sensors could be interfaced to the incumbent electro-optical sensor following this method, adapted to interpretation of the other new or updated sensors. The method further includes observing a condition of the spectrometer plasma emission signal corresponding to an endpoint condition and changing output of an optical interface emission source optically coupled to the incumbent electro-optical sensor, to signal the endpoint condition.

One aspect of this method is using a photo emitter as an optical interface emission source. Alternatively, an optical fiber can act as the optical interface emission source.

The method further may include differentiating response of the incumbent electro-optical sensor between the optical interface emission source and a plasma glow from the plasma glow region. This differentiating may include obstructing optical input from the plasma glow region to the incumbent electro-optical sensor. Alternatively, it may include fitting an interference or other filter to the incumbent electro-optical sensor.

This method further may include terminating or modifying processing of a layer of semiconductor device in the process chamber, corresponding to changing output of the optical interface emission source.

Another embodiment is a method of retrofitting a process chamber control system. The system includes a process chamber and an incumbent electro-optical sensor operably coupled to process controls. The method includes optically coupling an optical interface emission source to the incumbent electro-optical sensor and differentiating response of the incumbent electro-optical sensor between the optical interface emission source and a plasma glow from inside the process chamber. The method further includes, during processing in the process chamber, changing output of the optical interface emission source in response to changes in process conditions within the process chamber.

Aspects of the first method embodiment, described above, also may be applied to this embodiment.

A further embodiment is an optical interface adapter, adapted to interface to an incumbent electro-optical sensor that receives optical omissions from a plasma glow inside a process chamber. This adapter includes a mounting assembly, mechanically coupled between the incumbent electro-optical sensor and the process chamber. It includes an optical interface emission source, secured by a mounting assembly and optically coupled to the incumbent electro-optical sensor. It may include logic and resources, responsive to changing of process conditions in the process chamber, coupled to the optical interface emission source. Alternatively, this optical interface adapter may stand alone without the logic and resources, or it may further be combined with an automatic process control that is electrically coupled to and responsive to the incumbent electro-optical sensor and the optical interface adapter. The automatic process control further may be combined with a process chamber.

While the present invention is disclosed by reference to the preferred embodiments and examples detailed above, it is understood that these examples are intended in an illustrative rather than in a limiting sense. It is contemplated that modifications and combinations will readily occur to those skilled in the art, which modifications and combinations will be within the spirit of the invention and the scope of the following claims.

I claim:

1. A method of retrofitting a process chamber control system, the system including a process chamber and an incumbent electro-optical sensor that is optically coupled to a plasma glow region in the process chamber and operably coupled to process controls for the process chamber, the method including:

monitoring exhaust gasses from the process chamber in a device outside the process chamber, utilizing a spectrometer having a plasma generator and detecting at least one spectrometer plasma emission signal;

observing a condition of the spectrometer plasma emission signal corresponding to an endpoint condition; and changing output of an optical interface emission source optically coupled to the incumbent electro-optical sensor, to signal the endpoint condition.

2. The method of claim 1, wherein the optical interface emission source is a photo-emitter.

3. The method of claim 1, wherein the optical interface emission source is an optical fiber.

4. The method of claim 1, further including differentiating response of the incumbent electro-optical sensor between the optical interface emission source and a plasma glow from the plasma glow region.

5. The method of claim 4, wherein differentiating includes obstructing optical input from the plasma glow region to the incumbent electro-optical sensor.

6. The method of claim 4, wherein differentiating includes fitting an interference filter to the incumbent electro-optical sensor.

7. The method of claim 4, further including terminating or modifying processing of a layer of a semiconductor device in the process chamber, corresponding to the changing output of the optical interface emission source.

8. A method of retrofitting a process chamber control system, the system including a process chamber and an incumbent electro-optical sensor operably coupled to process controls, the method including:

optically coupling an optical interface emission source to the incumbent electro-optical sensor;

differentiating response of the incumbent electro-optical sensor between the optical interface emission source and a plasma glow from inside the process chamber; and during processing in the process chamber, changing output of the optical interface emission source in response to changes in process conditions within the process chamber.

9. The method of claim 8, wherein the optical interface emission source is a photo-emitter.

10. The method of claim 8, wherein the optical interface emission source is an optical fiber.

11. The method of claim 8, wherein differentiating includes obstructing optical input from the plasma glow inside the process chamber to the incumbent electro-optical sensor.

12. The method of claim 8, wherein differentiating includes fitting an interference filter to the incumbent electro-optical sensor.

13. The method of claim 8, further including terminating or modifying processing of a layer of a semiconductor device in the process chamber, corresponding to the changing output of the optical interface emission source.

* * * * *